United States Patent [19]

Kotera et al.

[11] Patent Number: 4,695,407
[45] Date of Patent: Sep. 22, 1987

[54] METHOD FOR PURIFYING 1-AMINOANTHRAQUINONE

[75] Inventors: Norio Kotera, Amagasaki; Masatoshi Uegaki, Nara; Masakatsu Yoshimura, Sakai; Shinzaburo Masaki, Ashiya; Tatsuo Kaneoya, Toyonaka; Takashi Miyaoka, Minoo; Yuzo Maegawa, Ibaraki; Akira Fukasawa, Niihama, all of Japan

[73] Assignee: Sumitomo Chemical Company, Limited, Osaka, Japan

[21] Appl. No.: 466,568

[22] Filed: Feb. 15, 1983

[30] Foreign Application Priority Data

Mar. 3, 1982 [JP] Japan ................................. 57-34169

[51] Int. Cl.$^4$ ............................................. C07C 97/24
[52] U.S. Cl. ................................................. 760/378
[58] Field of Search ........................................ 260/378

[56] References Cited

U.S. PATENT DOCUMENTS

| 2,738,354 | 3/1956 | Kern et al. | 260/378 |
| 3,907,828 | 9/1975 | Thiem et al. | 260/378 |
| 3,984,425 | 10/1976 | Mori et al. | 260/378 |
| 4,054,586 | 10/1977 | Hirai et al. | 260/378 |
| 4,323,431 | 4/1982 | Takahashi et al. | 260/378 |

Primary Examiner—Glennon H. Hollrah
Assistant Examiner—Raymond Covington
Attorney, Agent, or Firm—Stevens, Davis, Miller & Mosher

[57] ABSTRACT

A method for purifying 1-aminoanthraquinone which comprises previously subjecting a crude 1-aminoanthraquinone to a removal treatment of inorganic impurities so that their content is reduced to not more than 4 wt. % as converted to ash basis or to a removal treatment of iodine-consuming reductive inorganic impurities so that their content is reduced to not more than 2 wt. % as converted to consumed iodine basis, and then rectifying the 1-aminoanthraquinone.

7 Claims, No Drawings

METHOD FOR PURIFYING 1-AMINOANTHRAQUINONE

The present invention relates to a method for purifying 1-aminoanthraquinone. More particularly, the present invention relates to a method for purifying 1-aminoanthraquinone which comprises rectifying crude 1-aminoanthraquinone after inorganic impurities contained in it have been previously removed so that their content, as converted to ash basis, is reduced to not more than 4 wt.%, or after the iodine-consuming reductive inorganic impurities contained in it have been previously removed so that their content, as converted to consumed iodine basis, is reduced to not more than 2 wt.%.

1-Aminoanthraquinone is well known as an important intermediate for the production of anthraquinone dyes and the like, and there are known various methods for producing it. For example, anthraquinone is nitrated with concentrated nitric acid or a mixed acid and then reacted with ammonia or reduced with alkali sulfide and/or alkali hydrogensulfide.

The 1-Aminoanthraquinone thus obtained, however, contains various impurities and needs to be purified in order to obtain high-purity 1-aminoanthraquinone. Of the known various purification methods, rectification of crude 1-aminoanthraquinone may be said to be industrially advantageous as compared with other methods. Because 1-aminoanthraquinone is an organic compound which has a high melting point and boiling point as well as being very sensitive to temperature and violent in thermal decomposition, the operation of rectification is accompanied with many difficulties.

For the rectification of aminoanthraquinones, severe temperature control is necessary because, at the high-temperature molten state of aminoanthraquinones, the rate of thermal decomposition increases as the temperature increases, and high because the temperature which causes violent thermal decomposition which makes industrial operation substantially impossible is relatively close to the melting point. Further, in order to shorten the residence time at high temperatures as much as possible in the rectification system, it is preferred to minimize the capacity of each apparatus as well as shorten and simplify the layout of piping as much as possible.

Realizing that rectification was a method for purifying 1-aminoanthraquinone, the present inventors tried the rectification of 1-aminoanthraquinone with great attention paid to its physical properties. However, the invention still encountered many difficulties, such as blocking of the rectification system following the thermal decomposition. Thus, the present inventors, recognized that the problem of the thermal decomposition of 1-aminoanthraquinone should be solved in order to establish rectification as an industrial method. As a result of extensive study to inhibit the thermal decomposition of 1-aminoanthraquinone, the present inventors found that the content of inorganic impurities contained in crude 1-aminoanthraquinone, a starting material for rectification, largely affects the thermal decomposition of 1-aminoanthraquinone, thus rapidly increasing the rate of thermal decomposition. However, when the content is limited below a definite value, thermal decomposition is inhibited to a large extent, thus making it possible not only to keep the yield of 1-aminoanthraquinone in rectification high, but also to carry out the rectification in a very stable operation. The present invention was completed based on this finding.

According to the present invention, there is provided in the rectification of crude 1-aminoanthraquinone, a method for purifying 1-aminoanthraquinone characterized in that crude 1-aminoanthraquinone is rectified after inorganic impurities contained in it are previously removed so that their content, as converted to ash basis, is reduced to not more than 4 wt.%, or iodine-consuming reductive inorganic impurities contained in it are previously removed so that their content, as converted to consumed iodine basis, is reduced to not more than 2 wt.%.

Next, the present invention will be explained specifically.

Crude 1-aminoanthraquinone, an object of the present invention, is obtained by conventionally well-known methods, for example, by nitrating anthraquinone with concentrated nitric acid or a mixed acid and reacting the resulting 1-nitroanthraquinone with ammonia or reducing it with an alkali sulfide and/or an alkali hydrogensulfide. In these methods, contamination with impurities cannot be avoided, not excepting with inorganic impurities.

The inorganic impurities referred to herein are for example as follows: Alkali nitrate and alkali sulfate generated as a result of the neutralization of nitric acid and sulfuric acid used for nitration with a neutralizing agent; ammonium salts such as ammonium nitrite, etc., generated when ammonia is used in the reduction process alkali sulfide and alkali hydrogensulfide which remain when excess amounts of alkali sulfide and alkali hydrogensulfide are used as a reducing agent; alkali thiosulfate and alkali polysulfide generated as a result of the reduction; and alkali carbonate or alkali acetate contained as impurities in alkali sulfide and alkali hydrogensulfide used as a reducing agent.

For the purpose of this invention, alkali means alkali metal salts, alkaline earth metal salts or ammonium salts, and, specifically, salts of sodium, lithium, potassium, calcium, magnesium, beryllium, barium, ammonium, etc. In industry, however, alkali generally takes the form of sodium salt.

In rectifying 1-aminoanthraquinone containing these inorganic impurities, the present invention provides a method in which these inorganic impurities are previously removed so that their content, as converted to ash basis, is reduced to not more than 4 wt.%, preferably not more than 2 wt.%; or a method in which iodine-consuming reductive inorganic impurities are previously removed so that their content, as converted to consumed iodine basis, is reduced to not more than 2 wt.%, preferably not more than 1.2 wt.%. Various methods may be thought of for such removal treatment. As examples, the methods given below are advantageous on an industrial basis:

(1) Crude 1-aminoanthraquinone is filtered off on a vacuum filter and washed with water. The resulting crude 1-aminothraquinone wet cake is fluidized on a kneader or the like or slurried again with addition of water, and filtered off on a pressure filter to separate a crystal; and this crystal is then rectified.

(2) Crude 1-aminoanthraquinone is extracted with an organic solvent, whereby the inorganic impurities are transferred to an aqueous layer and then removed.

(3) Crude 1-aminoanthraquinone is treated with an oxidizing agent to oxidize iodine-consuming reductive inorganic compounds, whereby the amount of consumed iodine is reduced and the compounds are made harmless.

In addition to these, there is a method to repeat the washing of crude 1-aminoanthraquinone with large quantities of water and the like. This method is theoretically possible, but it is not very advantageous from the industrial point of view. It is of course possible, however, to employ this method if condition permits Next, the methods presented above will be explained more fully.

Crude 1-aminoanthraquinone, as obtained by the reduction of crude 1-nitroanthraquinone with alkali sulfide and alkali hydrogensulfide, is obtained as crystal. By filtering the reduction solution, the reduction waste liquor is separated. In this filtration treatment, breaking the large crystal of crude 1-aminoanthraquinone results in poor separation of the crude 1-aminoanthraquinone and the reduction waste liquor. In this filtration treatment, therefore, it was determined that it is very important in the filtration and washing efficiencies not to break the 1-aminoanthraquinone crystal.

After extensive studies in an effect to solve this problem, the present inventors found that the type of filtration is very important to the collapse of crystal, and that a method of using vaccum filters is most efficient in carrying out filtration without breaking the crystal.

The vacuum filter used in this case may be any of batch type ones and continuous type ones, but the latter is preferably used. As for continuous type vacuum filters, there are, for example, rotary drum type ones, rotary plate type ones, filter cloth horizontal travelling type ones and the like. These filters have a filtering section and washing section separated from each other, so that washing the reduction waste liquor away from the crude 1-aminoanthraquinone wet cake after filtration can efficiently be carried out at the washing section.

For washing the wet cake, the amount of water used for washing is generally 3 to 7 times by weight based on the crude 1-aminoanthraquinone. In this case, it is more preferred to use the water for washing in portions, preferably three or more portions than to use in one portion. Washings generated from the later-stage filter may be recycled for use in this stage.

Although the washing method is not particularly limited herein, it is effective to employ a method in which water for washing is sprinkled in a spray on the crude 1-aminoanthraquinone wet cake.

By this method, the reduction waste liquor can be separated from the surface of 1-aminoanthraquinone crystals leaving the crystal hardly broken. By this method, however, the reduction waste liquor entrapped in the crude 1-aminoanthraquinone crystal cannot sufficiently be removed. Therefore, in order to carry out the subsequent rectification process smoothly, said waste liquor should be removed to such a degree that inorganic impurities contained in it exert substantially no adverse effect on the rate of thermal decomposition on rectification described above.

As a result of a further study on this method, the present inventors found that, after removal of the reduction waste liquor by the vacuum filter, the entrapped reduction waste liquor in the resulting crude crystal of 1-aminoanthraquinone needs to be removed therefrom by breaking the crude crystal. For this purpose, it is very effective to filter the crude 1-aminoanthraquinone wet cake, as obtained by filtration and washing on the foregoing filter, by means of a pressure filter.

The pressure filter used in this case may be any of batch type ones and continuous type ones, but the latter is preferably used. Examples of continuous type pressure filters are rotary drum type ones, rotary plate type ones and the like. The rotary plate type ones are particularly useful because of their superior crystal-breaking effect and good washing efficiency. Supplying the crude 1-aminoanthraquinone wet cake which is such, as obtained by filtration and washing on the vacuum filter, to the pressure filter is generally difficult, depending upon the type of pressure filter. Further, in production on the industrial scale, it is very inconvenient to handle a solid as such. The present inventors thus made a further study on a method to connect the two filters. As a result, it was found that it is effective to fluidize said wet cake as such by kneading the cake on a batch type or continuous type kneader or converting it again to a slurry with addition of water, and then supplying the fluidized product to the pressure filter.

The former method makes use of the thixotropic property of crude 1-aminoanthraquinone itself. On kneading said wet cake on kneaders such as ribbon mixers, pug mill, double-arm type kneaders (e.g. dispersion type kneaders), readco-continuous kneaders, auger type extruders, etc., the wet cake comes to retain fluidity, so that it can be supplied to the pressure filter in a stable manner. In the case of the latter method, it is sufficient that the amount of water added is of such a degree that the wet cake can be slurried to gain fluidity.

By filtering the thus fluidized or slurried wet cake on the pressure filter, the 1-aminoanthraquinone crystal is broken, and the entrapped reduction waste liquor in said crystal can advantageously be removed.

The filtrate generated by such filtration on the pressure filter, particularly by filtration of the slurry produced with addition of water, may also be used in recycling as a liquor for washing on the preceding vacuum filter.

Next, the extraction treatment with organic solvents is a method in which an organic solvent is added to crude 1-aminoanthraquinone after reduction in order to transfer 1-aminothraquinone to the organic solvent layer. The reduction waste liquor layer (aqueous layer) is then separated from the 1-aminoanthraquinone, thereby removing the inorganic impurities.

The organic solvent usable is preferably one which dissolves crude 1-aminoanthraquinone but not the inorganic impurities. Additionally, it must not act to promote the decomposition of crude 1-aminoanthraquinone even on heating.

Examples of organic solvents which may satisfy the condition like this are benzene and naphthalene type aromatic hydrocarbons and their derivatives having the nucleus substituted with, for example, a halogen, e.g., fluorine, chlorine, bromine, amino, nitro, ether or sulfonalkyl group. Specific examples are benzene, toluene, o-, m- or p-xylene, ethylbenzene, cumen, n-propylbenzene, diethylbenzene, naphthalene, tetralin, methylnaphthalene, chlorobenzene, o-, m- or p-dichlorobenzene, 1,2,3- or 1,2,4-trichlorobenzene, isomeric dichlorotoluene, α- or β-chloronaphthalene, o-, m- or p-chloroaniline, anisole, chloroanisole and bromoanisole.

Preferred solvents of these are substituted benzenes such as toluene, xylene, chlorobenzene, dichlorobenzene, trichlorobenzene, anisole, chloroaniline and the like.

Said organic solvent may be mixed with crude nitroanthraquinone at the beginning of the reduction, or added after completion of the reduction. It is sufficient that the amount of the organic solvent used is one necessary to dissolve all 1-aminoanthraquinone contained in crude 1-aminoanthraquinone. In this case, generally, diaminoanthraquinones having a lower solubility than 1-aminoanthraquinone, e.g., 1,5-diaminoanthraquinone, 1,8-diaminoanthraquinone and the like, do not dissolve in the organic solvent to remain as a crystal in the system, so that separation of these undissolved products by filtration or the like is effective.

In this case, it is also possible to add additional amounts of organic solvent for the purpose of improving extraction efficiency.

The application of the extraction treatment in this manner results in most of the inorganic impurities being present in the aqueous layer. Therefore the inorganic impurities promoting the rate of thermal decomposition are not present or, if any, slighty present in the organic solvent containing dissolved 1-aminoanthraquinone. Consequently, 1-aminoanthraquinone can be rectified after removal of the organic solvent from the organic solvent layer.

The foregoing two methods exemplifying the removal of inorganic compounds themselves by physical means, while the third method renders said inorganic compounds harmless by chemical treatment.

Generally, crude 1-aminothraquinone favorably obtained by the industrial method contains 3 to 8 wt.%, as converted to consumed iodine basis, of iodine-consuming reductive inorganic compounds. In this method the above reductive inorganic impurities promoting the rate of thermal decomposition are chemically removed by oxidizing said impurities to make them harmless.

The content of the iodine-consuming reductive inorganic impurities converted to consumed iodine basis, which is referred to herein, is measured and calculated by the following procedure:

(1) About 50 g of crude 1-aminoanthraquinone is accurately weighed (W g), and mixed with 100 ml of water with stirring.
(2) The solution is suction-filtered through a No. 2 Whatman filter paper, and washed with 40 ml of water.
(3) The washing and the filtrate are combined and diluted to 100 ml with water (using 100-ml graduated flask).
(4) Ten ml of this liquor is transferred to a 100-ml Erlenmeyer flask, 10 ml of a N/100 $I_2$ is added, and after adding 2 drops of acetic acid, the mixture is allowed to stand for 20 minutes in a dark place.
(5) The liquor is titrated to the end point with a N/100 $Na_2S_2O_3$ ($A_1$ ml).
(6) A blank test is carried out with 10 ml of water ($A_2$ ml). The content of reductive inorganic impurities is converted to consumed iodine basis by the following formula:

$$\frac{1.27 \times (A_2 - A_1)}{W} \text{ (wt. \%)}$$

The value converted to ash basis, which is referred to herein, is a value obtained by the ash measurement method shown in JIS K 4101.

The oxidation can be carried out efficiently by reaction with an oxidizing agent represented by air, perhalogenates or hydrogen peroxide. Of these, oxidation with air is particularly advantageous in terms of economy.

Air-oxidation of the reductive inorganic impurities is generally carried out as follows. Air is introduced into the reaction mass after reduction with or without the presence of a catalyst represented by cobalt sulfate. Oxidation is carried out at generally 25° to 100° C., preferably 60° to 100° C. The reaction mass after reduction may be used for oxidation after once filtration-treated.

The air-oxidized reaction mass is filtered and dried to obtain crude 1-aminoanthraquinone. Thus, the reductive inorganic impurities in crude 1-aminoanthraquinone are oxidized to result in a reduction in the consumed iodine content of crude 1-aminoanthraquinone.

By applying the treatment as described above, the content of the inorganic impurities contained in crude 1-aminoanthraquinone can be reduced to not more than 4 wt.%, as converted to ash basis, or the content of the iodine-consuming reductive inorganic impurities contained therein can be reduced to not more than 2 wt.%, as converted to consumed iodine basis. As a result, the thermal decomposition of 1-aminoanthraquinone is much inhibited even by rectification thereof, and the rate of thermal decomposition slows down, whereby the rectification yield improves and the rectification operation can be carried out stably.

Of course, in the present invention, a method to reduce the content of the inorganic impurities to not more than the value described above, is not limited to those mentioned above, and other optional methods may be employed.

In the present invention, the reason for critically limiting the content of the inorganic impurities is as follows: When the content of organic impurities is higher than the value specified by the present invention, the thermal decomposition becomes violent and the rate of thermal decomposition quickens, thereby resulting in lower fields of rectification and an unstable rectification operation. When the content is in the range below the specified value, the points described above do not change to an extreme degree if the value of the content varies.

According to the method of the present invention, therefore, it is not always necessary to completely eliminate the inorganic impurities from crude 1-aminoanthraquinone, but it is sufficient to remove the impurities by the industrially usable methods as described above until the content decreases below at least the specified value. If so, the operation of the subsequent rectification becomes very advantageous industrially, so that the industrial value of the present invention is very high.

Next, the present invention will be illustrated with reference to the following examples.

EXAMPLE 1

A reduction mass obtained by the reduction of crude 1-nitroanthraquinone with sodium sulfide was filtered by a horizontal travelling type vacuum filter on a filter cloth, and the wet cake obtained was washed with water.

Washing with water was carried out by dividing water in a quantity six times by weight based on the crude 1-aminoanthraquinone into three portions, and spraying each portion on the crude 1-aminoanthraquinone cake from a spray nozzle. The crude 1-aminoanthraquinone obtained was dried. This product was designated as (A).

The crude 1-aminoanthraquinone, after washing with water, was slurried again with water in a quantity seven times by weight based on the crude 1-aminoanthraquinone, filtered on a rotary plate type pressure filter and dried. This product was designated as (B).

The content of inorganic impurities contained in this crude 1-aminoanthraquinone (B) was measured, and it was found that the content was 1.0 wt.%, as converted to ash basis.

This crude 1-aminoanthraquinone (B) was heated to 300° C. under nitrogen atmosphere. After the temperature reached 300° C., the crude 1-aminoanthraquinone remained under this same condition for 1 hour. The loss of 1-aminoanthraquinone during this period of 1 hour was 2.8 wt.%, which means that there was no effect on the rate of thermal decomposition of 1-aminoanthraquinone.

This crude 1-aminoanthraquinone (B) was rectified by the method disclosed in Example 1 of U.S. Pat. No. 4,323,431. It was found that the rectification could be carried out by a very stable operation.

COMPARATIVE EXAMPLE 1

The content of inorganic impurities contained in the crude 1-aminoanthraquinone (A) obtained in Example 1 was measured, and it was found that the content was 4.5 wt.%, as converted to ash basis.

This crude 1-aminoanthraquinone (A) was measured for thermal stability at 300° C. under nitrogen atmosphere, and it was found that the 1-aminoanthraquinone decomposed at a rate of 8.0 wt.% per hour. During this measurement, there were also observed the generation of ammonia odor and aqueous distillate following the thermal decomposition of 1-aminoanthraquinone.

This crude 1-aminoanthraquinone (A) was rectified by the same method as in Example 1, and as a result, it was found that: Piping parts were blocked by the thermal decomposition product of 1-aminoanthraquinone, so that stable feed of the melt by a feed pump was difficult; continuous withdrawal of the bottom liquor from the bottom of the thin-film evaporator could not be stably carried out because of the thermal decomposition product of 1-aminoanthraquinone; and therefore, the balance of the whole rectification system could not be kept. Rectification had to be stopped after about 30 minutes after beginning of the feed.

EXAMPLE 2

Crude 1-nitroanthraquinone (composition of organic substances: anthraquinone, 0.5 wt.%; 1-nitroanthraquinone, 82 wt.%; 2-nitroanthraquinone, 5 wt.%; 1,5-dinitroanthraquinone, 0.5 wt.%; other dinitroanthraquinones and others, 12 wt.%) was reacted with ammonia, and the reaction mass obtained was filtered to obtain crude 1-aminoanthraquinone wet cake.

This wet cake was washed with warm water (70° C.) of ten times by weight based on it, and then dried. The content of inorganic impurities contained in the crude 1-aminoanthraquinone (C) thus obtained was 5.5 wt.%, as converted to ash basis.

The crude 1-aminoanthraquinone (C) was slurried with the addition of warm water (70° C.) in an amount 20 times by weight based on the crude 1-aminoanthraquinone, followed by filtration and drying.

The content of inorganic impurities contained in the crude 1-aminoanthraquinone (D) thus obtained was 1.8 wt.%, as converted to ash basis.

Thus crude 1-aminoanthraquinone (D) was heated to 300° C. under nitrogen atmosphere. The content of 1-aminoanthraquinone at the time when the temperature reached 300° C. was 74.7 wt.%. Thereafter, the 1-aminoanthraquinone was kept at the same condition for 1 hour. The loss of 1-aminoanthraquinone content during this period of 1 hour was 2.9 wt.%, meaning that there was little effect on the rate of thermal decomposition of 1-aminoanthraquinone.

Rectification treatment

Crude 1-aminoanthraquinone (D) was continuously fed to an agitated melting vessel at a rate of 10 kg/hour and melted. The melt obtained was supplied by a feed pump to the bottom of a rectifying column. At a thin-film evaporator connected with the bottom of the column, a part of the fed melt was evaporated together with the reflux liquor from the column, and the bottom liquor was continuously withdrawn from the bottom of the evaporator out of the rectification system at a rate of 2.4 kg/hour.

The vapor generated in the thin-film evaporator was rectified in the rectifying column. A part of the vapor was partially condensed at the reflux condenser and allowed to flow down to the column. A part of the vapor from the reflux condenser was partially condensed via a partial condenser and withdrawn from the rectification system. The rest of the vapor was finally totally condensed and solidified at a vacuum rotary cooler and withdrawn out of the rectification system. All the distillate was obtained at an average discharge rate of 7.6 kg/hour.

The purity of 1-aminoanthraquinone was not less than 98.5 wt.%, and the recovery rate of 1-aminoanthraquinone at the rectification step was not less than 91%.

COMPARATIVE EXAMPLE 2

The crude 1-aminoanthraquinone (C) obtained in Example 2 was heated to 300° C. under nitrogen atmosphere after it was kept at the same condition for 1 hour, the content of 1-aminoanthraquinone was 66.2 wt.%. From this, it was found that the loss of 1-aminoanthraquinone content during this period of 1 hour was 8.5 wt.%, meaning that the loss was about three times that of the thoroughly washed product in Example 2.

The crude 1-aminoanthraquinone (C) was rectified under the same condition as in Example 2, but it was found that: Piping parts were blocked by the thermal decomposition product of 1-aminoanthraquinone, so that stable feed of the melt by a feed pump was difficult; and continuous withdrawal of the bottom liquor from the bottom of the thin-film evaporator could not be carried out in a stable manner because of the thermal decomposition product of 1-aminoanthraquinone.

On further continuing the rectification, violent vibrations resulted at the thin-film evaporator necessitating the stoppage of the rectification process. When the evaporator was disassembled, it was found that a large quantity of the thermal decomposition product adhered to the axial part of the evaporator, thus making it impossible to maintain proper balance.

EXAMPLE 3

After reduction of crude 1-nitroanthraquinone with sodium hydrogensulfide, o-chloroaniline in an amount 12 times by weight based on the crude 1-aminoanthraquinone was added. The crude 1-aminoanthraquinone was dissolved hot in the o-chloroaniline layer which was then separated from the aqueous layer by the liquid/liquid separation technique. Thereafter, the o-chloroaniline layer was washed with water of the same amount as the crude 1-aminoanthraquinone, and after being separated from the aqueous layer, it was flash-distilled under reduced pressure to distil out o-chloroaniline. The recovery rates of crude 1-aminoanthraquinone and 1-aminoanthraquinone by solvent extraction were 98% and 100%, respectively. The contents of inorganic impurities and o-chloroaniline contained in the crude 1-aminoanthraquinone thus obtained were 0.5 wt.%, as converted to ash basis, and 1.5 wt.%, respectively. On rectifying the crude 1-aminoanthraquinone in the same manner as in Example 1, the rectification could be carried out smoothly and in high yields to give high-purity 1-aminoanthraquinone stably.

EXAMPLE 4

After reduction of crude 1-nitroanthraquinone with sodium hydrogensulfide, the crude 1-aminoanthraquinone wet cake was collected by filtration. The crude 1-aminoanthraquinone was washed with warm water (40° C.) of ten times by weight based on it and dried. The composition or organic substances contained in the crude 1-aminoanthraquinone (E) thus obtained was as follows:
Anthraquinone: 0.7 wt.%
1-Aminoanthraquinone: 76.4 wt.%
2-Aminoanthraquinone: 2.0 wt.%
Diaminoanthraquinones: 11.8 wt.%
Other organic substances: 4.4 wt.%.

The content of iodine-consuming reductive inorganic impurities contained in this crude 1-aminoanthraquinone (E) was 3.2 wt.%, as converted to consumed iodine basis.

This crude 1-aminoanthraquinone (E) was slurried with an addition of warm water (70° C.) in an amount 20 times by weight based on crude 1-aminoanthraquinone, followed by filtration and drying.

The content of iodine-consuming reductive inorganic impurities contained in the crude 1-aminoanthraquinone (F) thus obtained was 0.9 wt.%, as converted to consumed iodine basis.

This crude 1-aminoanthraquinone (F) was heated to 300° C. under nitrogen atmosphere. The content of 1-aminoanthraquinone at that time was 74.7 wt.%. Thereafter, the crude 1-aminoanthraquinone was kept at the same condition for further 1 hour. The loss of 1-aminoanthraquinone content during this period of 1 hour was 2.8 wt.%, which means that there was little effect on the rate of thermal decomposition of 1-aminoanthraquinone.

Rectification treatment

Crude 1-aminoanthraquinone (F) was continuously fed to an agitated melting vessel at a rate of 10 kg/hour and melted. The melt obtained was supplied by a feed pump to the bottom of a rectifying column. At a thin-film evaporator connected with the bottom of the column, a part of the feed melt was evaporated together with the reflux liquor from the column, and the bottom liquor (composition: 1-aminoanthraquinone, 14.6 wt.%; 2-aminoanthraquinone, 1.1 wt.%; diaminoanthraquinones, 66.9 wt.%; and unknown substances and thermal decomposition products, 17.4 wt.%) was continuously withdrawn from the bottom of the evaporator out of the rectification system at a rate of 2.9 kg/hour.

The vapor generated in the thin-film evaporator was rectified in the rectifying column. A part of the vapor was partially condensed at the reflux condenser and allowed to flow down to the column. Another part of the vapor from the reflux condenser was partially condensed at a partial condenser and withdrawn out of the rectification system. The rest of the vapor was totally condensed finally and solidified at a vacuum rotary cooler and withdrawn out of the rectification system. All the distillate was obtained at an average discharge rate of 7.1 kg/hour. The average composition was as follows:
Anthraquinone: 1.0 wt.%
1-Aminoanthraquinone: 98.2 wt.%
2-Aminoanthraquinone: 0.8 wt.%.

COMPARATIVE EXAMPLE 3

The 1-aminoanthraquinone (E) obtained in Example 4 was heated to 300° C. under nitrogen atmosphere, and after it was kept at the same condition for further 1 hour, the content of 1-aminoanthraquinone was 65.6 wt.%. From this, it was found that the loss of 1-aminoanthraquinone content during this period of 1 hour was 9.1 wt.%, which means that the loss was about 3.3 times that of the thoroughly washed product in Example 4.

The crude 1-aminoanthraquinone (E) was rectified under the same condition as in Example 4, but it was found that: Piping parts were blocked by the thermal decomposition product of 1-aminoanthraquinone, so that stable feed of the melt by a feed pump was difficult; and continuous withdrawal of the bottom liquor from the bottom of the thin-film evaporator could not be carried out an a stable manner because of the thermal decomposition product of 1-aminoanthraquinone. Because of this, the balance of the whole rectification system could not be kept, and the rectification process had to be stopped about 20 minutes after beginning of the feed.

EXAMPLE 5

The reduction mass obtained in the same manner as in Example 4 was filtered and slurried again with water in an amount ten times by weight based on the crude 1-aminoanthraquinone obtained,. Thereafter, cobalt sulfate of 0.06 wt.% based on the slurry was added to the slurry, and air-oxidation was carried out at 100° C. for 3 hours. The slurry was then filtered and dried to obtain crude 1-aminoanthraquinone. The content of iodine-consuming reductive inorganic impurities was 0.8 wt.%, as converted to consumed iodine basis.

Rate of thermal decomposition

The crude 1-aminoanthraquinone obtained as above was measured for rate of thermal decomposition of 1-aminoanthraquinone by the method described in Example 1. It was found that the rate was 3.0 wt.%/hour at 300° C. On further rectification with this crude 1-aminoanthraquinone as material, the rectification could be carried out smoothly, in a stable manner and in high yields to give high-purity 1-aminoanthraquinone.

What is claimed is:

1. In a method for purifying crude 1-aminoanthraquinone containing inorganic impurities formed through nitration of anthraquinone with concentrated nitric acid or a mixed acid by rectification, the improvement comprising reducing said inorganic impurities to not more than 4 wt. % as converted to ash basis or reducing the iodine-consuming reductive inorganic impurities to not more than 2 wt. % as converted to consumed iodine basis prior to said rectification.

2. The method for purifying 1-aminoanthraquinone according to claim 1, wherein said removing comprises filtering off the crude 1-aminoanthraquinone to form a cake on a vacuum filter; washing the cake with water; fluidizing or slurrying the cake with addition of water; and filtering off a crystalline 1-aminoanthraquinone on a presure filter.

3. The method for purifying 1-aminoanthraquinone according to claim 1, wherein said removing is carried out by extracting the crude 1-aminoanthraquinone with an organic solvent to transfer the inorganic impurities to an aqueous layer.

4. The method for purifying 1-aminoanthraquinone according to claim 1, wherein said removing is carried out by oxidizing the inorganic impurities with an oxidizing agent to reduce the amount of consumed iodine.

5. The method for purifying 1-aminoanthraquinone according to claim 1, comprising reducing said inorganic impurities to not more than 2 wt.% as converted to ash basis.

6. The method for purifying 1-aminoanthraquinone according to claim 1, wherein the crude 1-aminoanthraquinone is obtained by nitrating anthraquinone with concentrated nitric acid or a mixed acid and reacting the resulting 1-nitroanthraquinone with ammonia or reducing it with an alkali sulfide and/or an alkali hydrogensulfide.

7. The method according to claim 1, comprising reducing said iodine-consuming reductive inorganic impurities to not more than 1.2 wt.% as converted to consumed iodine basis.

* * * * *